(12) United States Patent
Koren et al.

(10) Patent No.: US 7,553,272 B2
(45) Date of Patent: Jun. 30, 2009

(54) APPARATUS FOR GENERATING ELECTROMAGNETIC WAVEFORMS

(75) Inventors: Stanley A. Koren, Sudbury (CA);
Michael A. Persinger, Sudbury (CA);
Chin-Ning Chu, Antioch, CA (US);
Curt Allen Paulson, Antioch, CA (US)

(73) Assignee: Neurosciences Industries, Inc., Antioch, CA (US)

( * ) Notice: Subject to any disclaimer, the term of this patent is extended or adjusted under 35 U.S.C. 154(b) by 866 days.

(21) Appl. No.: 10/938,878

(22) Filed: Sep. 13, 2004

(65) Prior Publication Data
US 2006/0058571 A1   Mar. 16, 2006

(51) Int. Cl.
*A61N 2/04* (2006.01)

(52) U.S. Cl. ........................................ 600/13

(58) Field of Classification Search ............... 600/9–15; 128/897, 898
See application file for complete search history.

(56) References Cited

U.S. PATENT DOCUMENTS

| | | | | |
|---|---|---|---|---|
| 5,169,380 A | * | 12/1992 | Brennan | 600/26 |
| 5,314,400 A | * | 5/1994 | Tsyb et al. | 600/9 |
| 5,315,503 A | * | 5/1994 | Kato et al. | 700/87 |
| 5,330,410 A | * | 7/1994 | Baylink | 600/13 |
| 5,453,072 A | * | 9/1995 | Anninos et al. | 600/9 |
| 5,634,939 A | * | 6/1997 | Kuster et al. | 607/59 |
| 5,769,778 A | * | 6/1998 | Abrams et al. | 600/14 |
| 6,312,376 B1 | * | 11/2001 | Koren et al. | 600/13 |

* cited by examiner

*Primary Examiner*—Samuel G Gilbert
(74) *Attorney, Agent, or Firm*—Katten Muchin Rosenman LLP (57) ABSTRACT

An apparatus for generating electromagnetic waveforms to stimulate a subject includes a computing device generating digital waveform data. A digital-to-analog converter receives the digital waveform data from the computing device and generates a corresponding analog waveform signal. A channel selector having output channels is operable to apply the analog waveform signal to the output channels when the output channels are actuated. A sequencer independent of the computing device selects and actuates the output channels of the channel selector. An electromagnetic field generator is coupled to each output channel of the channel selector. The electromagnetic field generator coupled to each actuated output channel converts the analog waveform signal into an electromagnetic waveform thereby to expose a subject wearing the electromagnetic field generators to the electromagnetic waveform.

31 Claims, 9 Drawing Sheets

| BINARY | DECIMAL | DAC OUTPUT (VOLTS) |
|---|---|---|
| 11111111 | 255 | 5 |
| 01111111 | 127 | 0 |
| 00000000 | 0 | -5 |

Fig. 10

APPARATUS FOR GENERATING ELECTROMAGNETIC WAVEFORMS

FIELD OF THE INVENTION

The present invention relates to generally neuropsychology and in particular to an apparatus and method for generating electromagnetic waveforms to stimulate a subject.

BACKGROUND OF THE INVENTION

Diverse studies have shown that the behavioral, cellular and physiological functions of animals can be affected by magnetic stimuli. Weak magnetic fields exert a variety of biological effects ranging from alterations in cellular ion flux to modifications of animal orientation and learning, and therapeutic actions in humans. It is desirable to understand the effects of low intensity magnetic fields on humans as these magnetic fields are normally present in man-made environments. Devices and systems that emit such magnetic fields include telephones, headphones, computers and monitors, AC adapters, electrical fans, electric motors, hair dryers, cellular phones and other wireless communications devices, transmitter towers, power transmission lines and transformers, televisions, radios and compact disc (CD) players, to name but a few.

There are several theories addressing the mechanism of the effect that magnetic field exposure has on tissues. For example, low frequency magnetic field exposures have been proposed to exert their effect(s) through induction of electric currents. Although not widely believed, it has also been proposed that weak magnetic fields are detected by particles of magnetite in tissue and, by virtue of this detection, have a physiological effect.

Although the mechanism of the effects of magnetic field exposure on tissues is uncertain, it is clear that magnetic fields are a physical agent which have little attenuation in tissue and therefore, can be used to alter endogenous processes provided the magnetic fields can be detected and their detection coupled to a physiological process. In view of this, it is desired to expose subjects to magnetic fields to treat physiological, neurological and behavioral disorders and to determine the effect of a variety of magnetic stimuli on subjects.

An apparatus for generating electromagnetic waveforms to stimulate a subject is described in U.S. Pat. No. 6,312,376, to Koren et al. This apparatus includes an electromagnetic waveform signal generator that generates an analog waveform signal representing desired electromagnetic waveforms to be used to stimulate the subject. A selector is responsive to channel select input and applies the analog waveform signal to selected output channels of the selector. Electromagnetic field generators, coupled to the output channels of the selector, convert the analog waveform signal into electromagnetic waveforms thereby to expose the subject wearing the electromagnetic field generators to the desired electromagnetic waveforms. Although this apparatus works well, improvements in devices of this nature are desired.

It is therefore an object of the present invention to provide a novel apparatus and method for generating electromagnetic waveforms to stimulate a subject.

SUMMARY OF THE INVENTION

According to one aspect of the present invention there is provided an apparatus for generating electromagnetic waveforms to stimulate a subject, comprising:

a computing device generating digital waveform data;

a digital-to-analog converter receiving said digital waveform data from said computing device and generating a corresponding analog waveform signal;

a channel selector having output channels and operable to apply said analog waveform signal to said output channels when said output channels are actuated;

a sequencer independent of said computing device for selecting and actuating the output channels of said channel selector; and an electromagnetic field generator coupled to each output channel of said channel selector, the electromagnetic field generator coupled to each actuated output channel converting said analog waveform signal into an electromagnetic waveform thereby to expose a subject wearing said electromagnetic field generators to said electromagnetic waveform.

In one embodiment, only some of the output channels are selected and actuated by the sequencer at any given time. The order by which the output channels are selected and actuated by the sequencer is structured. In particular, the output channels of the channel selector are selected and actuated by the sequencer in succession. The sequencer selects and actuates the output channels so that the electromagnetic waveform to which the subject is exposed approximates rotational actions.

In another embodiment, the order by which the output channels of the channel selector are selected and actuated by the sequencer is random. The sequencer is adjustable to control the duration for which selected output channels remain actuated. The duration the sequencer maintains selected output channels actuated is random.

In one embodiment, the sequencer includes a timer for generating timing data and a selector circuit responsive to the timing data for selecting and actuating the output panels. The selector circuit counts output pulses generated by the timer and uses the count to control selection and actuation of the output channels. The timer is adjustable to modify the frequency of the output pulses. The timer includes a switch to condition the timer between different output pulse frequency modes.

According to another aspect of the present invention, there is provided an apparatus for generating electromagnetic waveforms to stimulate a subject, comprising:

a computing device generating digital waveform data;

a digital-to-analog converter receiving said digital waveform data from said computing device and generating a corresponding analog waveform signal;

a channel selector having an input receiving said analog waveform signal and a plurality of output channels, said channel selector being responsive to selection signals to select one or more output channels on which said analog waveform signal is applied;

a sequencer independent of said computing device generating said selection signals; and an electromagnetic field generator coupled to each output channel of said channel selector, the electromagnetic field generator coupled to each selected output channel converting said analog waveform signal into an electromagnetic waveform thereby to expose a subject wearing said electromagnetic field generators to said electromagnetic waveform.

According to a yet another aspect of the present invention, there is provided an apparatus for generating electromagnetic waveforms to stimulate a subject, comprising:

a computing device for generating digital waveform data, said computing device executing a real-time operating system;

a digital-to-analog converter for receiving said digital waveform data from said computing device and generating an analog waveform signal therefrom;

a channel selector having output channels and operable to apply said analog waveform signal to said output channels when said output channels are actuated; and a sequencer for selecting and actuating at least one of said output channels of said channel selector; and electromagnetic field generators coupled to said output channels of said channel selector, the electromagnetic field generators coupled to said selected output channels converting said analog waveform signal into an electromagnetic waveform thereby to expose a subject wearing said electromagnetic field generators to electromagnetic waveform.

In one embodiment, the real-time operating system is DOS. In another embodiment, the real-time operating system is non-graphical.

According to still yet another of the present invention, there is provided a method of stimulating a subject with electromagnetic waveforms, comprising:

generating digital waveform data via a computing device, said computing device having memory for storing at least one waveform definition file comprising a set of data representative of an electromagnetic waveform to be generated;

converting said digital waveform data to an analog waveform signal;

activating one or more channels of a channel selector via a sequencer, said sequencer being independent of said computing device;

applying said analog waveform signal to said one or more activated channels; and converting the analog waveform signal applied to each activated channels into an electromagnetic waveform via at least one electromagnetic field generator such that a subject wearing said electromagnetic field generators is subjected to said electromagnetic waveform.

The present invention provides advantages in that complex patterns of electromagnetic waveforms can be applied to a subject without introducing undesirable latency to the generation of the electromagnetic waveforms. This is achieved by employing a sequencer to control output channel selection and timing that is independent of the computing device used to generate the digital waveform data corresponding to the electromagnetic waveforms to be applied to the subject. The present invention provides further advantages in that the effect of latency associated with various computing platforms is also reduced.

BRIEF DESCRIPTION OF THE DRAWINGS

An embodiment of the present invention will now be described more fully with reference to the accompanying drawings in which:

FIG. 9b is an illustration of an analog conversion of the digital representation of FIG. 9a.

DETAILED DESCRIPTION OF THE INVENTION

Figure 1:
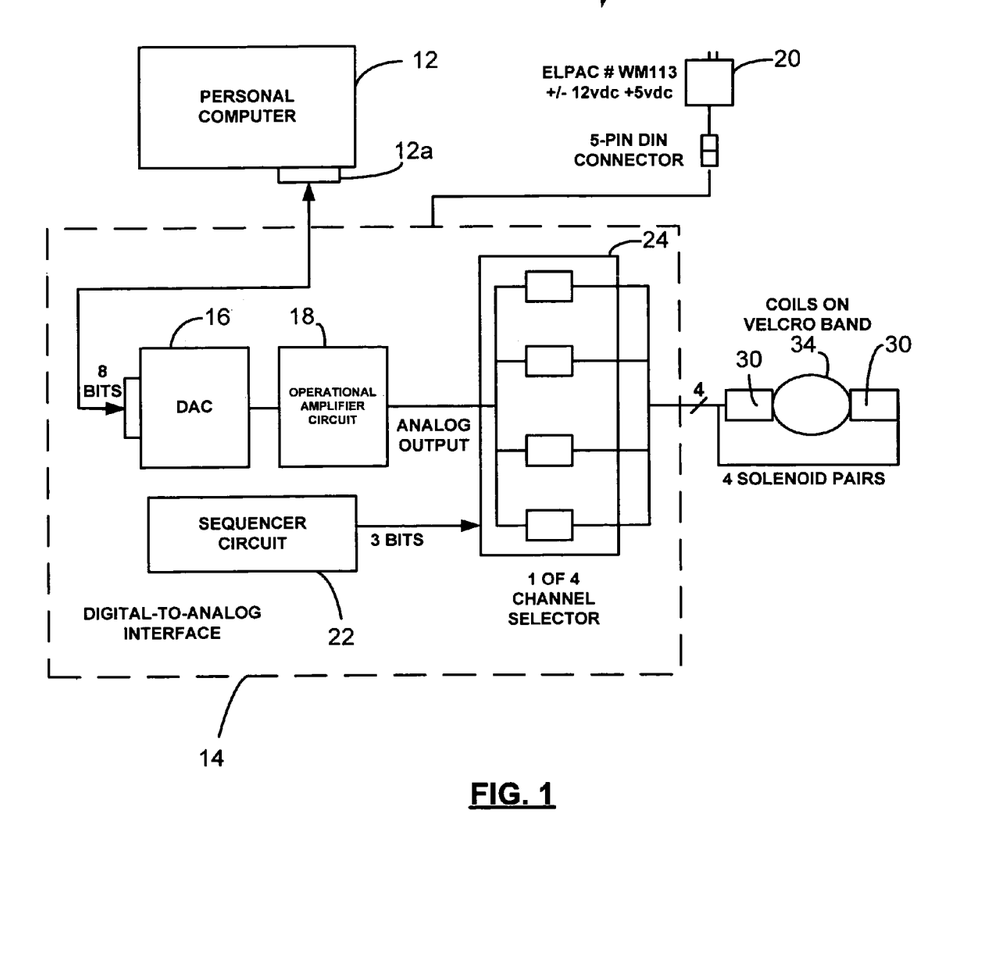
FIG. 1 is a schematic diagram of an apparatus for generating electromagnetic waveforms in accordance with the present invention.

Referring now to FIG. 1, an apparatus for generating electromagnetic waveforms to stimulate a subject is shown and is generally identified by reference numeral 10. As can be seen, apparatus 10 includes a processing unit in the form of a personal computer 12. Connected to a parallel port 12a of the personal computer 12 is a digital-to-analog interface 14. Digital-to-analog interface 14 includes an 8-bit digital-to-analog (DAC) converting stage 16, a two-stage direct coupled operational amplifier circuit 18, a sequencer circuit 22 and a channel selector 24. The channel selector 24 is responsive to selection signals generated by the sequencer circuit 22 to select the output channel on which analog waveform signals are to be directed. The components of the digital-to-analog interface 14 are powered by an ELPAC WM113 DC power supply 20. Power supply 20 provides +/−12v direct current (dc) output at 300 mA and +5v dc output at 860 mA. An electromagnetic field generator comprising a pair of solenoid assemblies 30 is coupled to each output channel of the channel selector 24 resulting in a total of four pair of solenoid assemblies 30. The solenoid assemblies 30 are mounted on a headband 34 with the solenoid assemblies 30 of each pair being positioned on the headband 34 at diametrically opposite locations.

Figure 2:
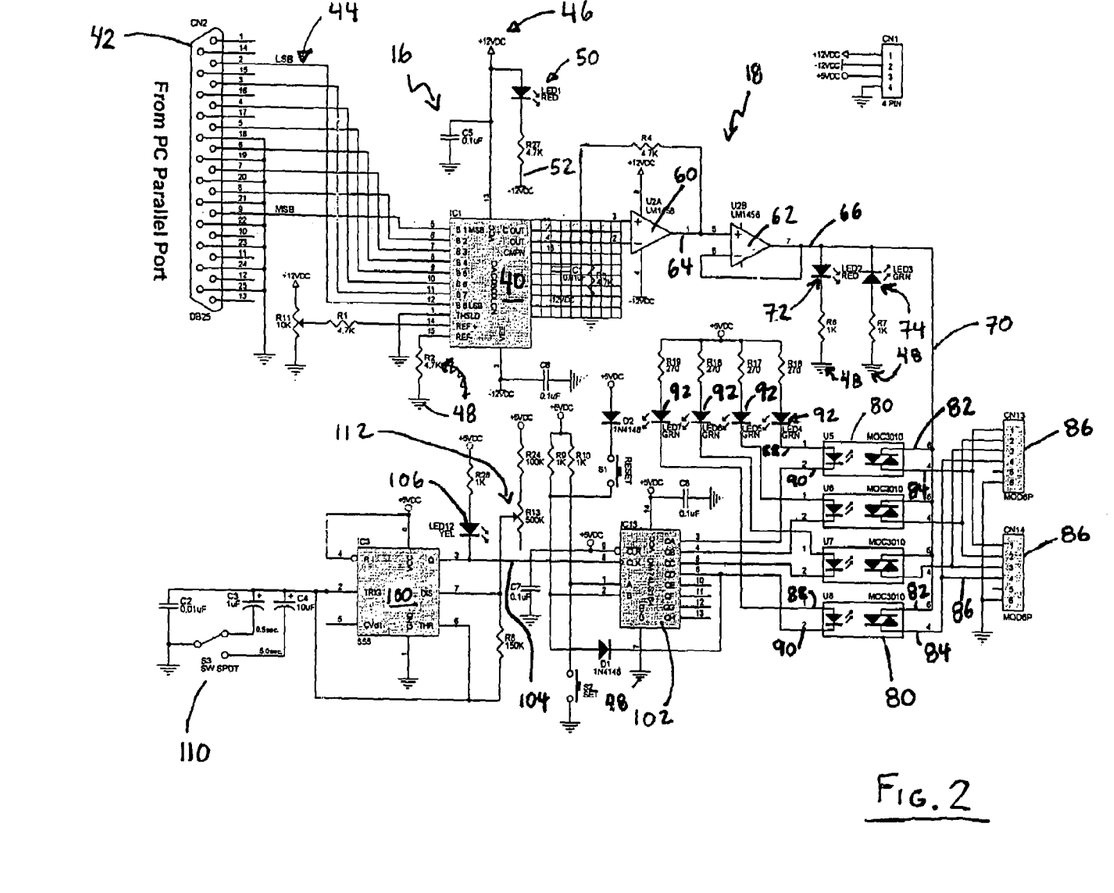
FIG. 2 is a schematic diagram of a digital-to-analog interface forming part of the apparatus of FIG. 1.
Figure 3:
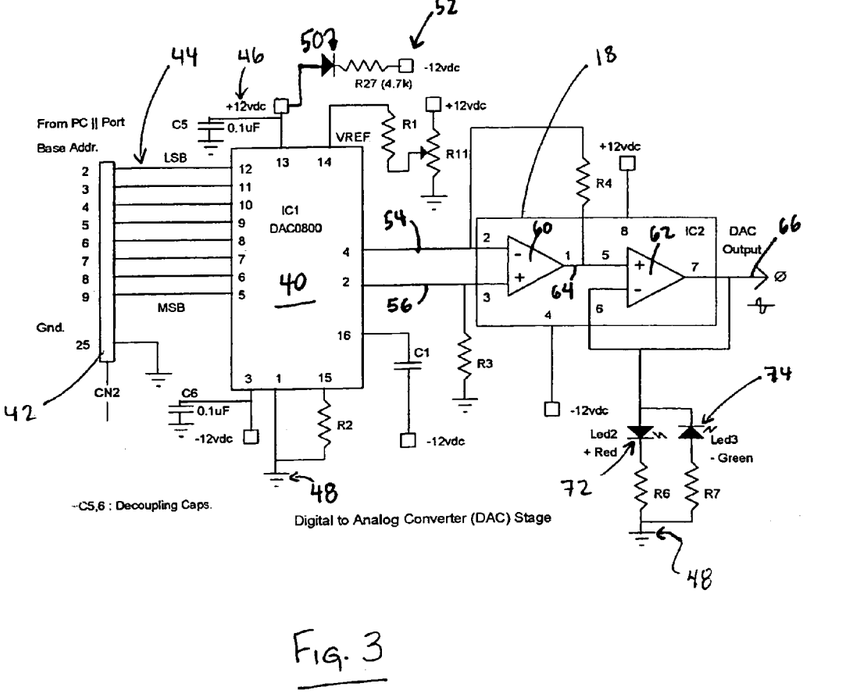
FIG. 3 is a schematic diagram of a digital-to-analog converter and an operational amplifier circuit forming part of the digital-to-analog interface of FIG. 2.

FIGS. 2 and 3 best illustrate the digital-to-analog converting stage 16 and operational amplifier circuit 18. The digital-to-analog converting stage 16 includes a digital-to-analog converter 40 such as that manufactured by National Semiconductor under part No. DAC0800LCN. The digital-to-analog converter 40 is coupled to port 12a of computer 12 via a parallel port connector 42 and a bus 44. The digital-to-analog converter 40 is also coupled to the +12v output of the power supply 20 via positive power input line 46 as well as to ground 48. A power-on light emitting diode (LED) 50 is coupled to the positive power input line 46 and to a negative power input line 52 extending to the −12v output of power supply 20 via resistor R27. Power-on LED 50 illuminates when the digital-to-analog interface 14 is in a powered "on" state.

The output leads 54 and 56 of the digital-to-analog converter 40 are connected to the operational amplifier circuit 18. The operational amplifier circuit 18 utilizes a pair of LM741CN operational amplifiers 60 and 62. Specifically, output leads 54 and 56 are coupled to the inverting and non-inverting terminals of operational amplifier 60. The output terminal 64 of operational amplifier 60 is coupled to the non-inverting terminal of operational amplifier 62. The output terminal 66 of operational amplifier 62 is fed back to its inverting terminal and also leads to an analog waveform output line 70. Red and green polarity LEDs 72 and 74 are coupled between the output terminal 66 and ground 48 through resistors R6 and R7 respectively. LEDs 72 and 74 provide a visual indication of the polarity of analog waveform signals output by the operational amplifier circuit 18.

Figure 4:
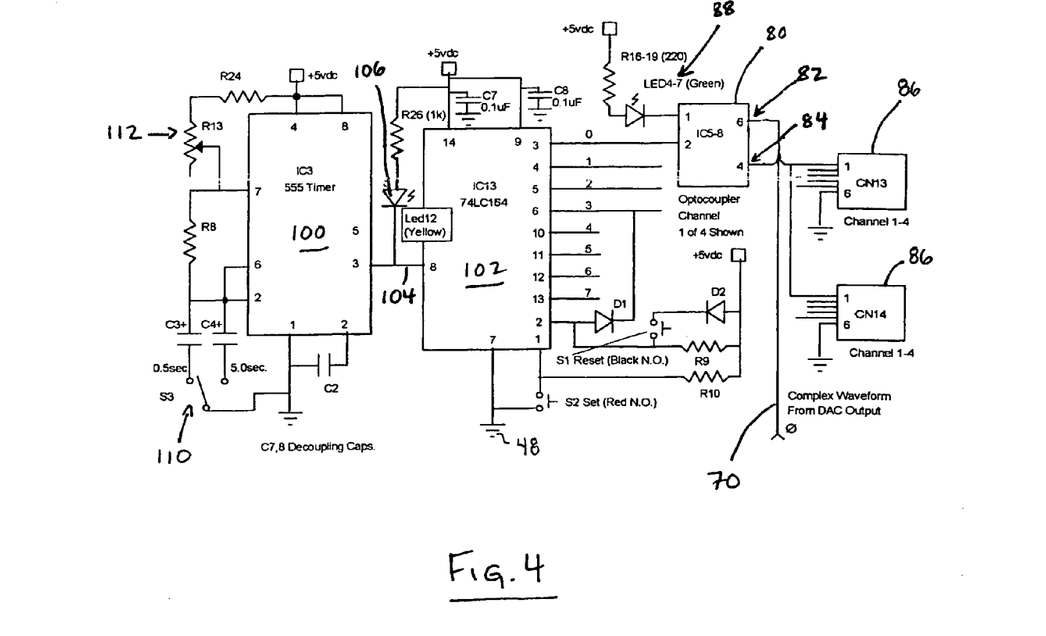
FIG. 4 is a schematic diagram of a sequencer circuit and a channel selector forming part of the digital-to-analog interface of FIG. 2.
Figure 5A:
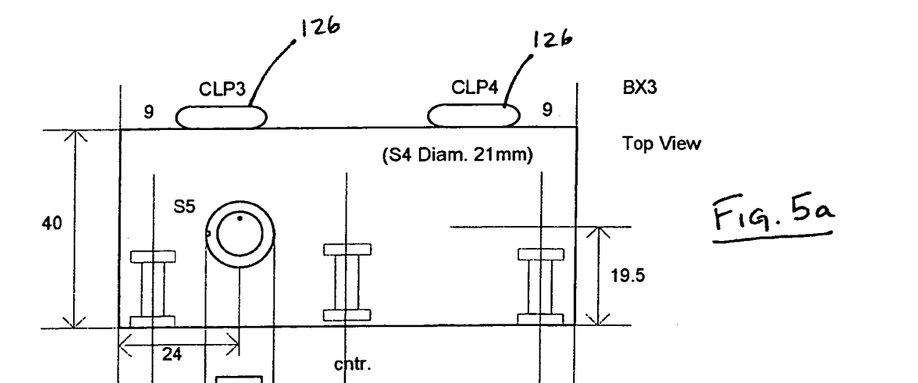
FIGS. 5a to 5c are top, side and bottom views of one solenoid assembly forming part of a pair of solenoid assemblies.
Figure 5B:
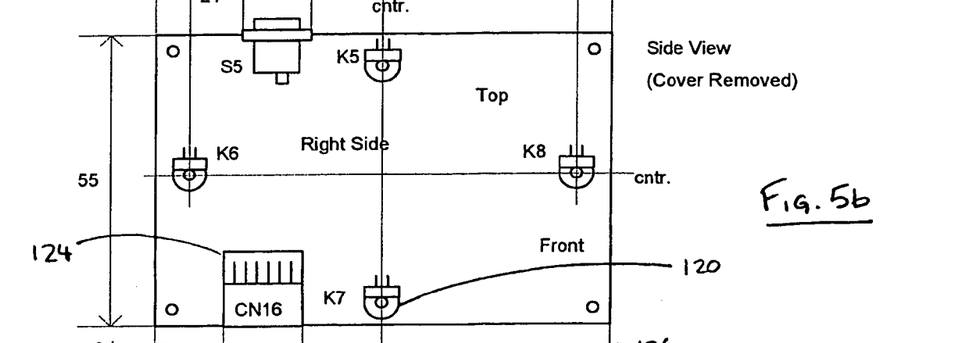
Figure 5C:
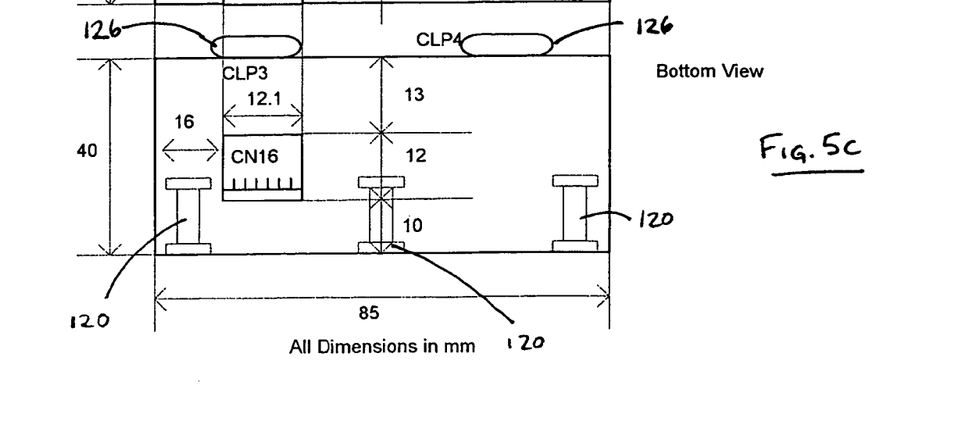
Figure 6A:
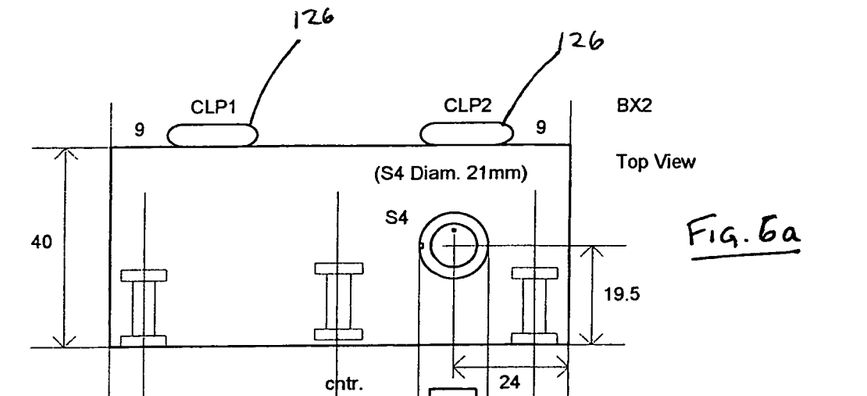
FIGS. 6a to 6c are top, side and bottom views of a second solenoid assembly forming part of the pair of solenoid assemblies.
Figure 6B:
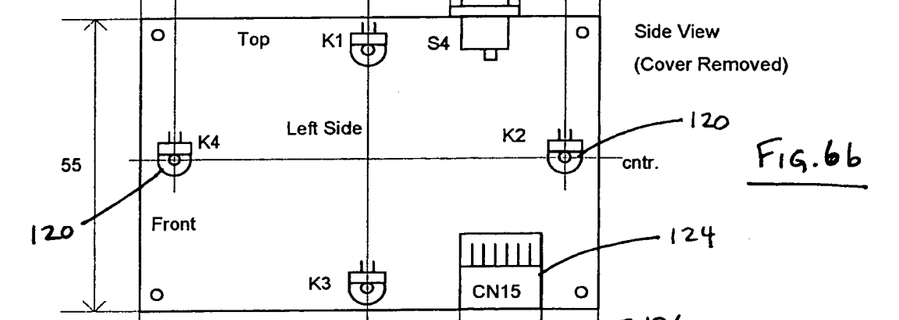
Figure 6C:
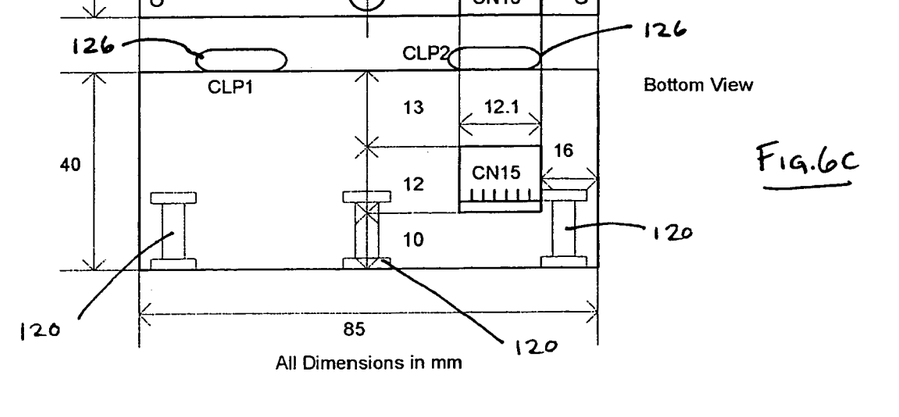
Figure 7A:
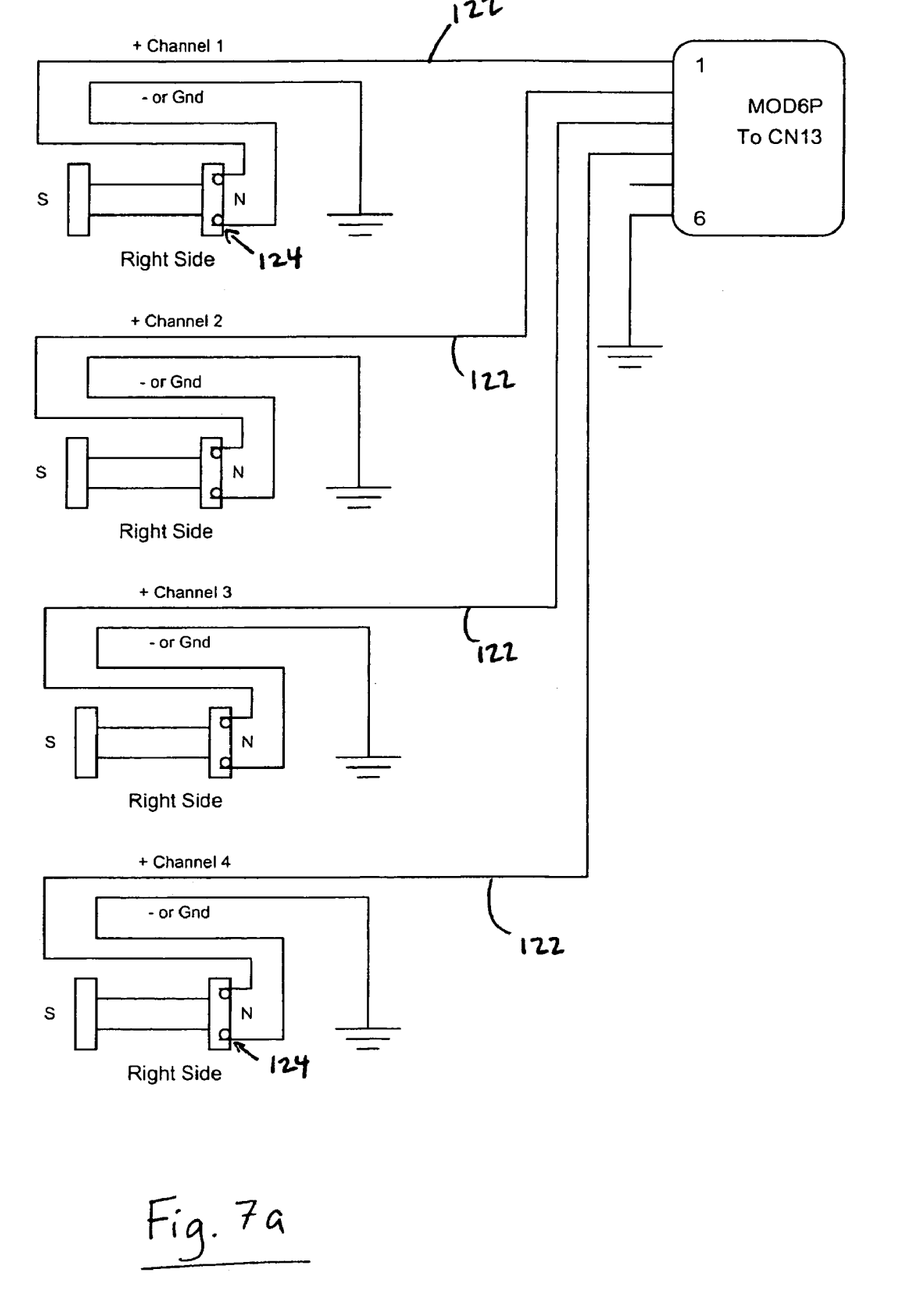
FIG. 7a is a schematic representation showing one solenoid assembly of each pair coupled to a channel connector.
Figure 7B:
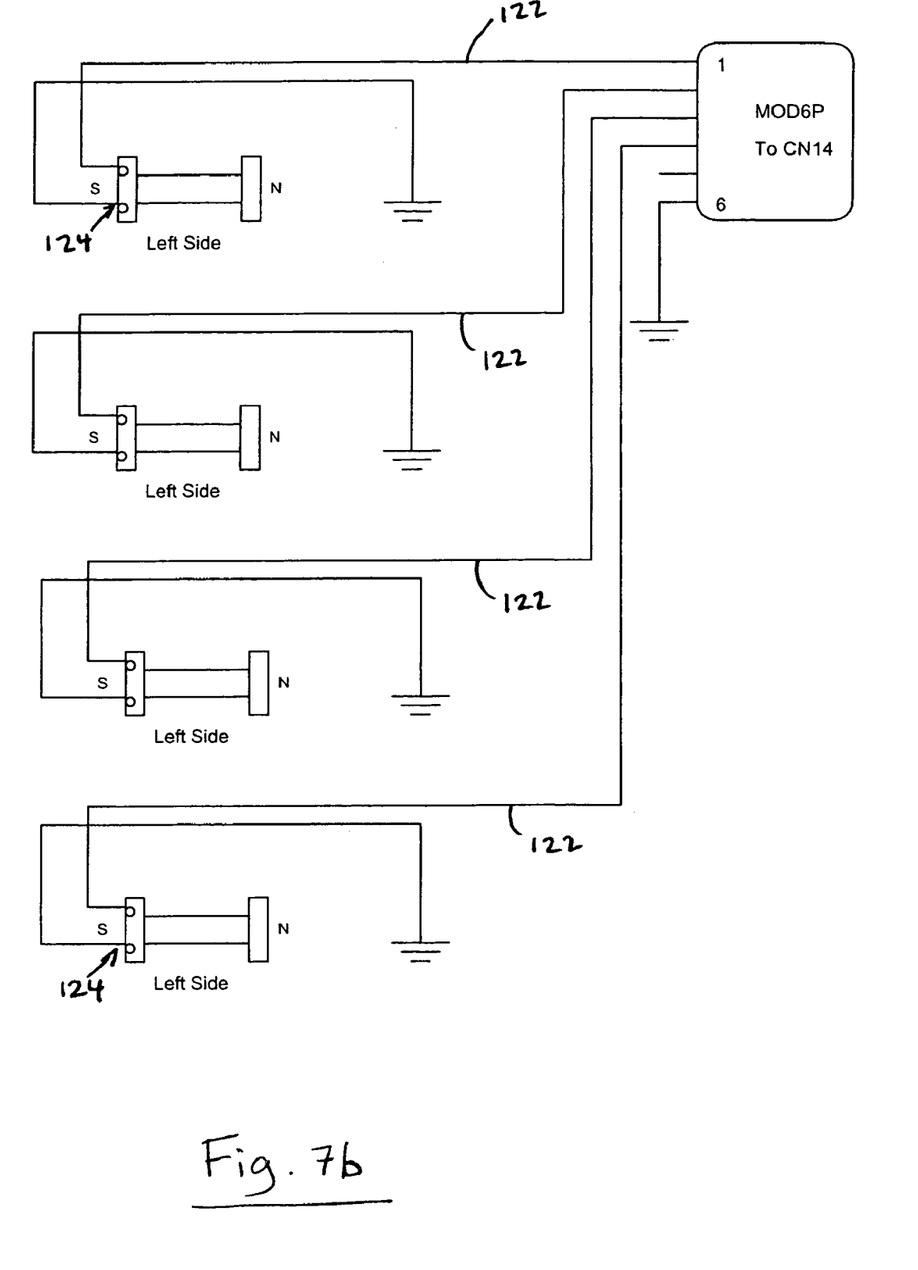
FIG. 7b is a schematic representation showing the other solenoid assembly of each pair coupled to a channel connector.

The channel selector 24 and sequencer circuit 22 are best illustrated in FIGS. 2 and 4. As can be seen, channel selector 24 includes four opto-couplers 80, each associated with an individual output channel of the channel selector 24. Each opto-coupler 80 has an input terminal 82 coupled to the analog waveform output line 70 and an output terminal 84 coupled to a pair of channel connectors 86 to which the opto-coupler's associated pair of solenoid assemblies 30 is connected. Each opto-coupler 80 also has a pair of drive terminals 88 and 90. One drive terminal 88 of each pair is coupled to the +5v output of power supply 20 via an LED 92. The other drive terminal 90 of each pair is coupled to the sequencer circuit 22. The sequencer circuit 22 selectively connects the drive terminals 90 to ground 48 to actuate the opto-couplers 80. When an opto-coupler 80 is actuated the opto-coupler 80 couples the analog wavefrom output line 70 to its output terminal 84 and hence, to its associated pair of solenoid assemblies 30. The associated LED 92 also illuminates to visually identify the active output channel of the channel selector 24.

The sequencer circuit 22 includes a timer 100 and a selector circuit 102 coupled to the timer 100 via line 104. The selector circuit 102 is a four-channel commutator that is coupled to the drive terminals 90 of each opto-coupler 80 and selectively couples one of the drive terminals 90 to ground 48 in response to the timer output. In this embodiment, the selector circuit 102 actuates the opto-couplers 80 in succession (i.e. in a structured order) in response to the output of the timer 100. In particular, the selector circuit 102 counts output logic high pulses generated by the timer 100 and applied to line 104. When the pulse count reaches a threshold number, the selector circuit 102 deactivates the active opto-coupler 80 and actuates the next opto-coupler 80.

An LED 106 is connected to line 104 and to the +5v dc of the power supply 20. A set switch 110 and a variable resistor 112 are coupled to the timer 100 to enable the frequency of the timer to be adjusted. In this embodiment, set switch 110 is actuable between two positions to condition the timer 100 to output a square wave at one of two fixed frequencies, namely 12 cycles per minute and 120 cycles per minute. The LED 106 flashes to provide a visual indication of the frequency of the output square wave generated by the timer 100. Since the selector circuit 102 uses a logic high pulse count to change the active channel of the channel selector 24, the frequency of the output square wave generated by the timer 100 controls the amount of time each opto-coupler 80 remains actuated (i.e. the sequence interval of the channel selector 24)

FIGS. 5a to 6c show the solenoid assemblies 30 forming one of the four pairs. As best seen in FIGS. 5b and 6b, each solenoid assembly 30 includes four solenoids 120 arranged in a diamond pattern. The solenoids 120 are constructed from a reed relay (Intertan 275-232) with the reed switch removed and replaced by a steel nail core that serves as a flux concentrator. The maximum power output of each solenoid 120 in the solenoid assembly 30 is limited to a maximum of 100 milliwatts (E=5 volts; R=250 ohms; I=20 milliamps; power=$I^2 \times R$=$(0.02A)^2 \times 250W$=100 milliwatts). As shown in FIGS. 5a to 7, the solenoid assemblies 30 are connected to a shielded cable 122 via a cable interface 124. Shielded cable 122 is connected to the channel connectors 86 thereby to couple the solenoid assemblies 30 to the output channel of its associated opto-coupler 80.

Figure 8:
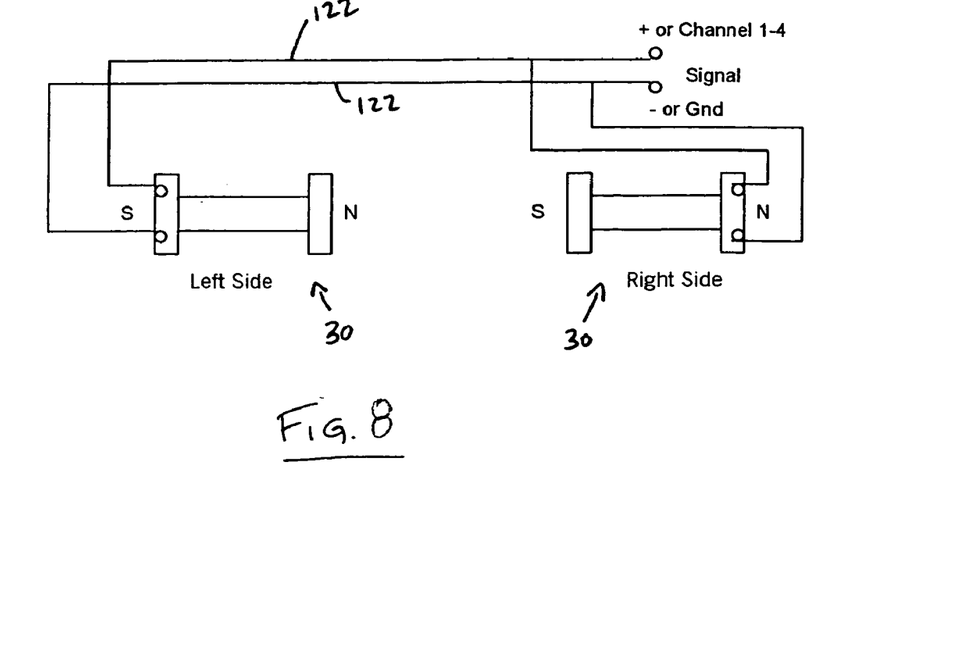
FIG. 8 is a schematic diagram showing one pair of solenoid assemblies.

The orientation of the electrical connections between the opto-couplers 80 and the solenoid assemblies 30 are such that some of the pairs of solenoid assemblies 30 are in phase (i.e. the solenoid assemblies are connected in North-to-North magnetic polarity) and some of the pairs of solenoid assemblies 30 are out of phase (i.e. the solenoid assemblies are connected in North-to-South magnetic polarity) as shown in FIG. 8. The solenoid assemblies 30 are attached to the headband 34 via a pair of clips 126, and are oriented so that their opposing polarities are aligned so as to provide a complete magnetic circuit. Adjacent solenoid assemblies 30 are separated by a distance equal to approximately 0.8 inches. The physical housing for the solenoid assemblies 30 can be varied provided the physical spacing between and geometry of the solenoid assemblies 30 is maintained. The solenoid assemblies 30 and the headband 34 are designed to allow attachment and landmarking on subjects.

Figure 9A:
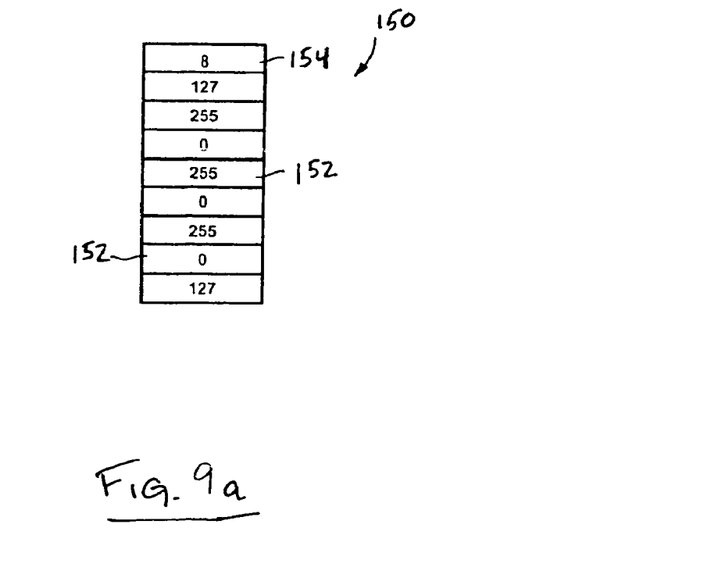
FIG. 9a is a table of points along a digital representation of an electromagnetic waveform forming a waveform definition file.
Figure 9B:
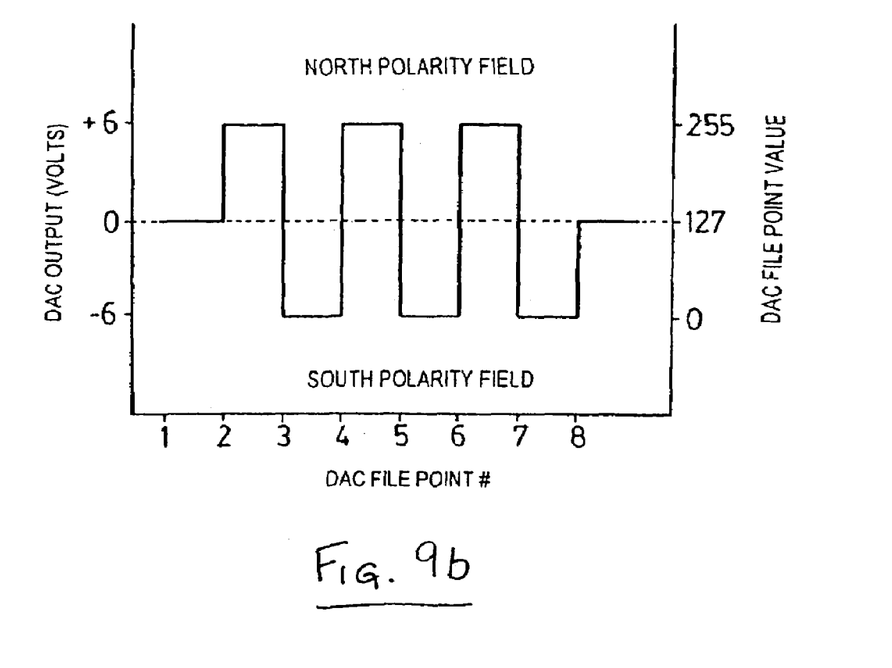

The electromagnetic waveforms to which subjects are to be exposed are digitally stored in the personal computer 12 as DAC files 150 (see FIG. 9a) and can be derived from mathematical equations, spoken words or custom designed. Each DAC file 150 includes a list of individual points 152 representing points along the corresponding electromagnetic waveform together with a header 154 indicating the number of individual points that are stored in the DAC file 150. The DAC file 150 is either in the form of a DOS-text file or an ASCII-text file with one individual point entry per line. Each individual point has a value in the range of 0 to 255 represented as an 8-bit binary number. FIGS. 9a and 9b illustrate an example of a DAC file 150 that is a digital representation of an electromagnetic square waveform as well as its analog equivalent. As can be seen, the DAC file header 154 indicates that eight individual points 152 are in the DAC file 150.

Figure 10:
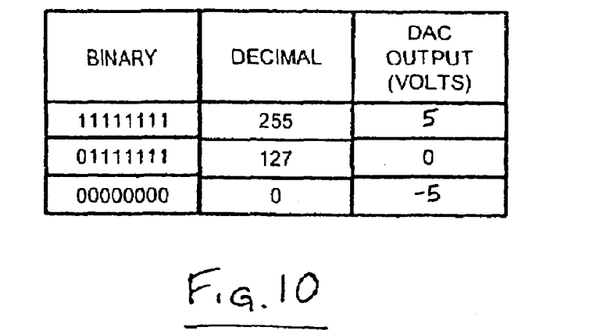
FIG. 10 is a table showing a digital-to-analog conversion of points along a digital representation of an electromagnetic waveform.

The value assigned to each individual point in a DAC file corresponds to an analog output voltage. FIG. 10 shows the conversion of individual point values to analog voltage levels. As can be seen, value 255 (binary "11111111") corresponds to an analog voltage equal to 5 volts, value 127 (binary "01111111") corresponds to an analog voltage equal to 0 volts, and value 0 (binary "00000000") corresponds to an analog voltage equal to −5 volts. By sequencing a set of points, via the DAC file 150, that is associated with a particular waveform, the computer 12 can produce an approximation of virtually any waveform within the limits of its storage and timing capabilities.

Stored within the personal computer 12 is a computer program which, when executed, outputs digital waveform data corresponding to the points in the DAC files 150 to the digital-to-analog interface 14. The computer program allows a user to select the form of the electromagnetic waveforms to be used to stimulate the subject either by creating DAC files or by selecting DAC files from a library of previously-built DAC files. Once a DAC file 150 has been selected, the computer program allows the user to assign values to a number of parameters associated with the selected electromagnetic waveform to be generated. These parameters include:

(i) the delay between each individual point of an electromagnetic waveform being generated (i.e. set the frequency of the electromagnetic waveform);
(ii) the number of times the electromagnetic waveform is to be repeated (i.e. the sequence limit); and
(iii) the time delay, in milliseconds, between each repeat of the electromagnetic waveform.

In order to accurately control the timing of electromagnetic stimuli provided to the subject, the digital waveform data corresponding to the points in the selected DAC file 150 are output by the computer 12 with precise timing. Presently, the computer program is written in Borland's Turbo Pascal Version 5.5 and Turbo Pascal Graphics Toolbox and run atop Microsoft DOS version 6.22. Microsoft DOS is a dedicated, single-process, real-time operating system; that is, an operating system that guarantees a certain capability within a specified time constraint, such as the precisely timed generation and output of digital waveform data.

Microsoft Windows operating systems have a graphical user interface and are multi-threaded with "soft" priorities being associated with the threads. As a result, processing resources are shared amongst a number of processes all executing simultaneously. It has been found that when running the computer program on Microsoft Windows platforms, inherent timing disturbances in the operating system, as well as the programming language used to create the computer program, can inhibit the computer 12 from outputting the digital waveform data in a precisely-timed manner. The dedicated, single-process focus of the non-graphical Microsoft DOS provides for more predictable digital instruction processing and information delivery. This is enhanced by the use of a low-level programming language such as Borland Turbo Pascal.

The source code for the Borland Turbo Pascal computer program is presented in Appendix A.

The operation of the apparatus 20 will now be described.. Initially, the operator selects the DAC files 150 representing the desired electromagnetic waveforms to which a subject is to be exposed. Once the operator has selected the DAC files to be output, the operator assigns values to the parameters for the electromagnetic waveforms to be generated thereby to establish the frequency of the electromagnetic waveforms, the sequence limit of each electromagnetic waveform and the time delay between electromagnetic waveform repeats.

Once the parameters have been assigned values, the headband 34 is placed on the head of a subject. The computer program is then conditioned to process each selected DAC file 150. As each DAC file is being processed, the personal computer 12 outputs the individual points in the DAC file, with the set delays therebetween, as 8-bit binary values to the digital-to-analog interface 14 via the parallel port 12a.

The digital-to-analog converter 40 in response to each received binary value generates a corresponding analog waveform signal that is output to the operational amplifier circuit 18. The operational amplifier circuit 18 in turn amplifies the analog waveform signal to the desired level according to its set gain. The output of the operational amplifier circuit 18 is conveyed to the channel selector 24 via the analog waveform output line 70.

At the same time, the timer 100 of the sequencer circuit 22 is conditioned to output the square wave on line 104 at the frequency determined by its setting. As mentioned previously, the selector circuit 102 in response to the square wave actuates the first opto-coupler 80 of the channel selection 24 and begins counting the logic high pulses of the square wave. When the count reaches the threshold number, the active opto-coupler is deactivated, the next opto-coupler 80 is actuated and the count is reset. The selector circuit 102 then begins counting the logic high pulse again. This process continues resulting in the output channels of the channel selector 24 becoming active in succession.

As the channel selector 24 receives the analog waveform signal transmitted by the operational amplifier circuit 18, the analog waveform signal is applied to all of the opto-couplers 80. The actuated opto-coupler 80, in turn, directs the analog waveform signal to its associated pair of solenoid assemblies 30. The solenoid assemblies 30 connected to the actuated opto-coupler 80 convert the received analog waveform signal into an equivalent electromagnetic (EM) signal thereby to stimulate the subject.

As the analog waveform signal is applied to each pair of solenoid assemblies 30, they are driven to expose the subject wearing the headband 34 to the desired electromagnetic waveforms. The manner by which the sequencer circuit 22 causes the channel selector 24 to cycle through its active output channel is selected so that the output electromagnetic waveforms approximate rotational actions hypothesized to add a complex derivative and chaotic components deemed necessary for enhanced brain stimulation.

In order to ensure that the apparatus operates as desired, typically prior to use, the apparatus 10 is calibrated to ensure that the minimum, maximum and median voltages of the analog waveform signals output by the operational amplifier circuit 18 are as desired. The calibration for each of these voltages is initiated by loading calibration DAC files into the personal computer 12 representing flat line waveforms at the minimum, maximum and median voltage levels. Once the calibration DAC files are loaded, the computer program is conditioned to process each calibration DAC file and output 8-bit binary values corresponding to the individual points therein to the digital to analog interface 14.

In response to the received binary values for each calibration DAC file, the DAC converting stage 16 in conjunction with the operational amplifier circuit 18 generate a constant voltage corresponding to the calibration DAC file. A DC voltmeter is coupled between the output terminal 66 and ground 48 to measure the output voltage. The gain of the operational amplifier circuit 18 is then adjusted until the measured output voltage corresponds with the voltage level represented by the calibration DAC file being processed. This procedure may have to be performed a number of times until the three measured output voltages correspond with the calibration DAC files within an acceptable margin of error. In the present embodiment, the minimum and maximum voltages are set to −5 volts and 5 volts respectively and the acceptable margin of error is 1%. The parameters assigned to the calibration DAC files are a delay between individual points of 1 millisecond, a sequence limit of 240 cycles, and a delay between cycles of 0 milliseconds.

The sequencer circuit 22 is also calibrated to ensure the timer 100 provides an output square wave at the desired frequency. This is achieved by setting the set switch 110 to the appropriate position (i.e. 0.5 seconds or 5.0 seconds), counting the number of flashes of the LED 106 that occur within a one-minute period, and then adjusting the variable resistor 112, which acts as a fine-tuning control, until the frequency of the timer 100 is at the desired frequency.

While the invention has been described with a degree of specificity, other configurations will occur to those of skill in the art. For example, in some scenarios, it may be desirable to model further complexity in the brain stimulation applied. Accordingly, the sequencer circuit can be adapted to select and activate multiple output channels of the channel selector simultaneously. If desired, parameter passing and batch processing can be used to expose the subject to a series of different electromagnetic waveforms for different durations and on different channels. Further, the number of output channels and solenoid assembly pairs can be altered to accommodate desired brain stimulation models.

Where randomness in the channel selection is desired, a random sequencer circuit to activate output channels of the channel selector can be used in place of the commutator. In this case, the random sequencer circuit randomly activates output channels of the channel selector and/or randomly alters the duration each output channel of the channel selector remains active By controlling the gain of the operational amplifier circuit, the nature and assigned parameters of the DAC files as well as the sequence interval, physiologists will appreciate that a subject can be exposed to various electromagnetic waveforms of various strengths and various frequencies.

Rather than using a sequencer circuit, including a timer and a selector circuit, those of skill in the art will understand that various other sequencers may be substituted without significantly affecting the working of the invention. For example, a second computing device can be used to for actuate one or more channels of the channel selector.

While solenoids are described to generate electromagnetic fields, other types of electromagnetic field generators will occur to those skilled in the art.

Other computing devices known to those skilled in the art that are capable of generating suitably regular digital waveform data can be employed to provide the digital waveform data to the digital-to-analog interface 14, including personal digital assistants, mobile phones, etc. Further, various components of the apparatus can be integrated into a single unit.

The computer program can be written using any low-level programming language that can be compiled to produce code that, when executed, does not suffer from timing irregularities that may adversely impact the reliability of the results of experiments performed with such apparatuses.

Instead of receiving input via DAC files, the computer program can accept a vector of parameters allowing a DOS batch program to run sequences of different waveforms and parameters as test stimulus over extended periods of time.

Although embodiments of the present invention has been described, those of skill in the art will appreciate that variations and modifications may be made without departing from the spirit and scope thereof as defined by the appended claims.

What is claimed is:

1. An apparatus for generating electromagnetic waveforms to stimulate a subject, comprising:
    a computing device generating digital waveform data;
    a digital-to-analog converter receiving said digital waveform data from said computing device and generating a corresponding analog waveform signal;
    a channel selector having output channels and operable to apply said analog waveform signal to said output channels when said output channels are actuated;
    a sequencer independent of said computing device, said sequencer comprising a timer for generating timing data, a selector circuit responsive to said timing data for selecting and actuating the output channels of said channel selector and a switch to condition said timer between different output pulse frequency modes; and
    an electromagnetic field generator coupled to each output channel of said channel selector, the electromagnetic field generator coupled to each actuated output channel converting said analog waveform signal into an electromagnetic waveform thereby to expose a subject wearing said electromagnetic field generators to said electromagnetic waveform.

2. An apparatus according to claim 1 wherein only some of said output channels are selected and actuated by said sequencer at any given time.

3. An apparatus according to claim 2 wherein the order by which output channels are selected and actuated by said sequencer is structured.

4. An apparatus according to claim 3 wherein only one output channel is selected and actuated at a time, output channels of said channel selector being selected and actuated by said sequencer in succession.

5. An apparatus according to claim 4 wherein said sequencer selects and actuates the output channels so that the electromagnetic waveform to which said subject is exposed approximates rotational actions.

6. An apparatus according to claim 4 wherein said sequencer is adjustable to control the duration for which selected output channels remain actuated.

7. An apparatus according to claim 3 wherein said sequencer selects and actuates the output channels so that the electromagnetic waveform to which said subject is exposed approximates rotational actions.

8. An apparatus according to claim 3 wherein said sequencer is adjustable to control the duration for which selected output channels remain actuated.

9. An apparatus according to claim 2 wherein the order by which output channels are selected and actuated by said sequencer is random.

10. An apparatus according to claim 9 wherein said sequencer is adjustable to control the duration for which selected output channels remain actuated.

11. An apparatus according to claim 9 wherein the duration the sequencer maintains selected output channels actuated is random.

12. An apparatus according to claim 2, wherein said sequencer includes a commutator.

13. An apparatus according to claim 1 wherein said selector circuit counts output pulses generated by said timer and uses said count to control selection and actuation of said output channels.

14. An apparatus according to claim 13 wherein the order by which output channels are selected and actuated by said sequencer is structured.

15. An apparatus according to claim 14 wherein only one output channel is selected and actuated at a time, output channels of said channel selector being selected and actuated by said sequencer in succession.

16. An apparatus according to claim 15 wherein said sequencer selects and actuates the output channels so that the electromagnetic waveform to which said subject is exposed approximates rotational actions.

17. An apparatus according to claim 13, wherein said timer includes a calibration circuit to permit the frequency of said output pulses to be adjusted.

18. An apparatus according to claim 13, wherein said timer includes an indicator providing a visual indication of the output pulse frequency.

19. An apparatus according to claim 1, wherein said computing device executes a real-time operating system.

20. An apparatus according to claim 19, wherein said real-time operating system is DOS.

21. An apparatus according to claim 19, wherein said real-time operating system is non-graphical.

22. An apparatus for generating electromagnetic waveforms to stimulate a subject, comprising:
    a computing device generating digital waveform data;
    a digital-to-analog converter receiving said digital waveform data from said computing device and generating a corresponding analog waveform signal;
    a channel selector having an input receiving said analog waveform signal and a plurality of output channels, said channel selector being responsive to selection signals to select one or more output channels on which said analog waveform signal is applied;

a sequencer independent of said computing device generating said selection signals, said sequencer comprising a timer for generating timing data, a selector circuit responsive to said timing data and generating said selection signals and a calibration circuit to permit the frequency of said timing data to be adjusted; and an electromagnetic field generator coupled to each output channel of said channel selector, the electromagnetic field generator coupled to each selected output channel converting said analog waveform signal into an electromagnetic waveform thereby to expose a subject wearing said electromagnetic field generators to said electromagnetic waveform.

23. An apparatus according to claim 22 wherein the order by which output channels are selected by said sequencer is structured.

24. An apparatus according to claim 23 wherein said sequencer selects the output channels so that the electromagnetic waveform to which said subject is exposed approximates rotational actions.

25. An apparatus according to claim 24 wherein only one output channel is selected at a time, output channels of said channel selector being selected by said sequencer in succession.

26. An apparatus according to claim 25 wherein said sequencer is adjustable to control the duration for which selected output channels remain active.

27. An apparatus according to claim 22 wherein the order by which output channels are selected by said sequencer is random.

28. An apparatus according to claim 27 wherein said sequencer is adjustable to control the duration for which selected output channels remain active.

29. An apparatus according to claim 28 wherein the duration the sequencer maintains selected output channels actuated is random.

30. An apparatus according to claim 22, wherein said computing device executes a real-time operating system.

31. An apparatus according to claim 30, wherein said real-time operating system is non-graphical.

* * * * *